US006685733B1

(12) United States Patent
Dae et al.

(10) Patent No.: US 6,685,733 B1
(45) Date of Patent: Feb. 3, 2004

(54) METHODS AND SYSTEMS FOR REDUCING SUBSTANCE-INDUCED RENAL DAMAGE

(75) Inventors: Michael W. Dae, Belmont, CA (US); Phillip Hopper, San Carlos, CA (US)

(73) Assignee: Radiant Medical, Inc., Redwood City, CA (US)

( * ) Notice: Subject to any disclaimer, the term of this patent is extended or adjusted under 35 U.S.C. 154(b) by 0 days.

(21) Appl. No.: 10/120,167

(22) Filed: Apr. 10, 2002

(51) Int. Cl.$^7$ ................................................. A61F 7/00
(52) U.S. Cl. ........................ 607/105; 607/106; 607/113
(58) Field of Search ........................... 607/96, 104–106, 607/113

(56) References Cited

U.S. PATENT DOCUMENTS

| | | | |
|---|---|---|---|
| 5,486,208 A | 1/1996 | Ginsburg | |
| 5,624,392 A | 4/1997 | Saab | |
| 5,957,963 A | 9/1999 | Dobak, III | |
| 6,110,168 A | 8/2000 | Ginsburg | |
| 6,231,594 B1 | 5/2001 | Dae | |
| 6,238,428 B1 | 5/2001 | Werneth et al. | |
| 6,245,095 B1 | 6/2001 | Dobak, III et al. | |
| 6,264,679 B1 | 7/2001 | Keller et al. | |

OTHER PUBLICATIONS

Zager, Richard A., Gmur, Dennis J., Bredl, Charles R., and Eng, Mary J., "Degree and Time Sequence of Hypothermic Protection Against Experimental Ischmic Acute Renal Failure", *Circulation Research*, pp. 1263–1269, vol. 65, No. 5.

Deray, Gilbert M.D., Bagnissl Corinne, M.D., Jacquaid, Claude, PhD, Dubois, Michele PhD, Adabra, Yvette, PhD, and Jaudon, Chantal, PhD. "Renal Effects of Low and Isoosmolar COntrast Media on Renal Hemodynamic in a Normal and Ischemic Dog Kidney", *Investigative Radiology*, pp. 1–4, vol. 34, No. 1.

Korr, Kenneth S. and Reitman, Arthur, "Renal Implications of Percutaneous Coronary Intervention", *Seminars in Nephrology*, pp. 36–46, vol. 21, No. 1 (Jan. 2001).

Heyman, Samuel Noah M.D., Reichman, James M.D., and Brezis, Mayer M.D., "Pathophysiology of Radiocontrast Nephropathy", *Investigative Radiology*, pp. 685–691, vol. 34, No. 11.

Gerlach, Anthony T. Pharm. D., and Pickworth, Kerry K. "Contrast Medium–Induced Nephrotoxicity: Pathophysiology and Prevention", pp. 540–548, *Pharmacotherapy*, vol. 20, No. 5.

(List continued on next page.)

*Primary Examiner*—Roy D. Gibson
(74) *Attorney, Agent, or Firm*—Robert D. Buyan; Stout, Uxa, Buyan & Mullins, LLP.

(57) ABSTRACT

Methods for reducing kidney damage induced by radiographic contrast medium or another nephrotoxic drug or substance administered to or generated by a patient include reducing the temperature of the patient by positioning an endovascular heat exchange device in a blood vessel of the patient and adjusting the temperature of the device to cause a reduction in the patient's temperature. The patient's temperature may be reduced prior to, during, and/or after, the administration of the contrast medium. The methods may also include administering an anti-shivering mechanism to the patient to reduce shivering caused by the reduction in the patient's temperature. The methods may also include disrupting the laminarity of blood flow around the device to enhance the temperature exchange between the device and the blood flowing around the device. The endovascular heat exchange device may be an endovascular heat exchange catheter. The device may be a component of a system, which includes a temperature controller in communication with the endovascular heat exchange device to reduce the temperature of the patient to reduce the temperature of the patient's kidneys.

49 Claims, 10 Drawing Sheets

OTHER PUBLICATIONS

Baker, et al. "Prevention of contrast nephropathy after cardiac catherisation", *Heart*, pp. 361–362, vol. 85.

Gruberg, Luis M.D., Mintz, Gary S M.D., et al. "The Prognostic Implications of Further Renal Function Deterioration Within 48 h of Interventional Coronary Procedures in Patients With Pre–existent Chronic Renal Insufficiency", pp. 1542–1548, Journal of the American College of Cardiology, vol. 36, No. 5.

Stevens, Melissa A M.D.,McCullough, Peter A M.D., et al. "A Prospective Randomized Trial of Prevention Measures in Patients at High Risk for Contrast Nephropathy", pp. 403–411, Journal of the American College of Cardiology, vol. 33, No. 2.

Thatte, Lalita M.D., and Vaamonde, Carlos A. M.D., "Drug–induced naphrotoxicity", Postgraduate Medicine, http://www.postgradmed.com/issues/1996/12_96/thatte.htm., Vol 100, No. 6, Dec. 1996.

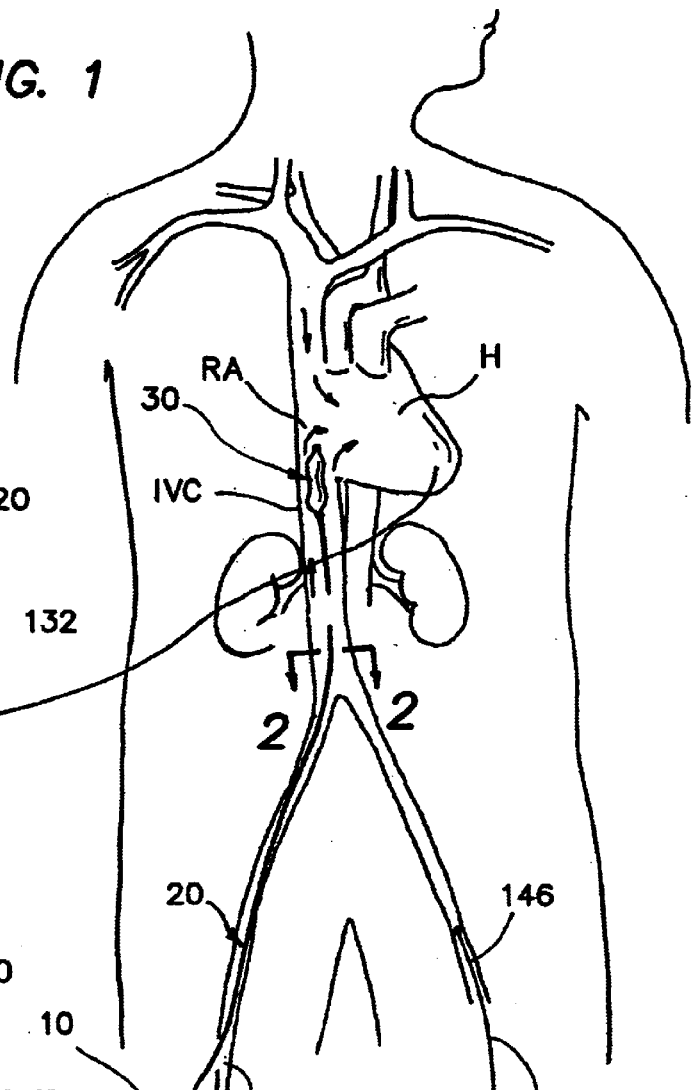
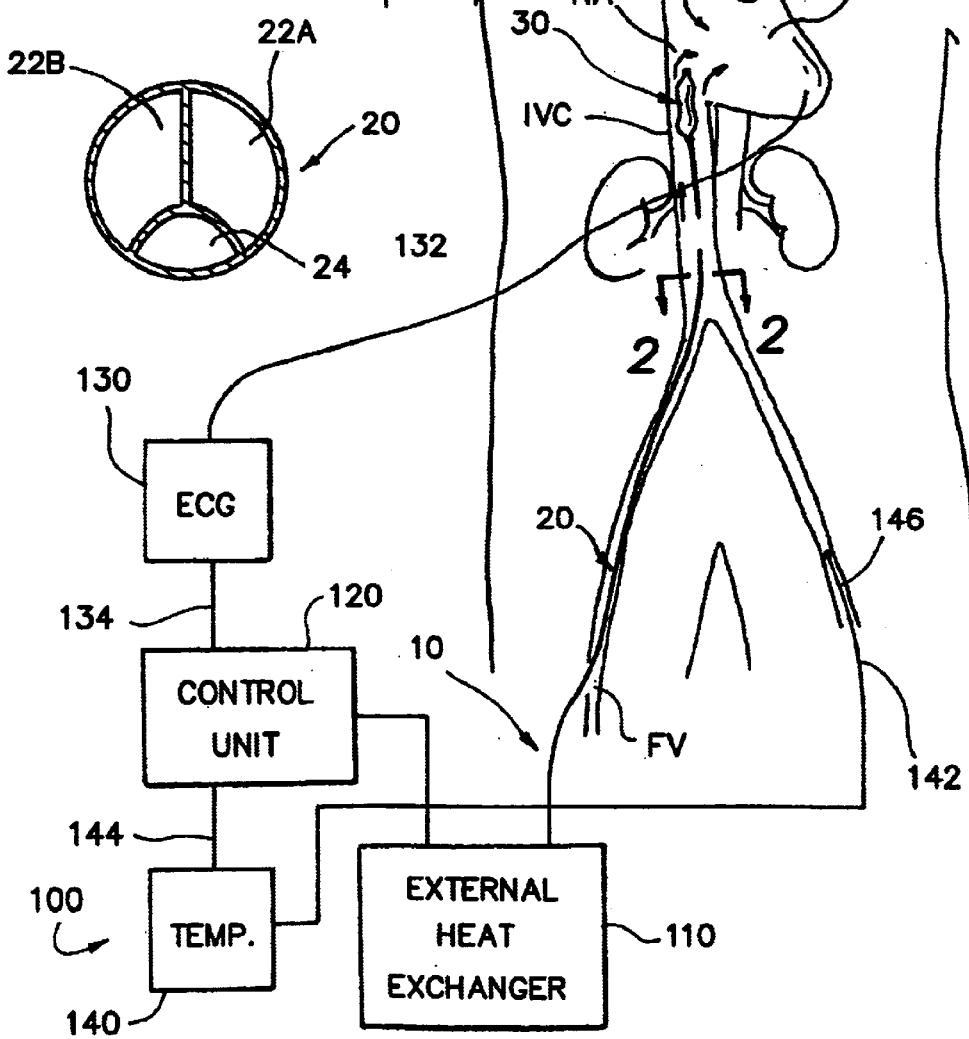

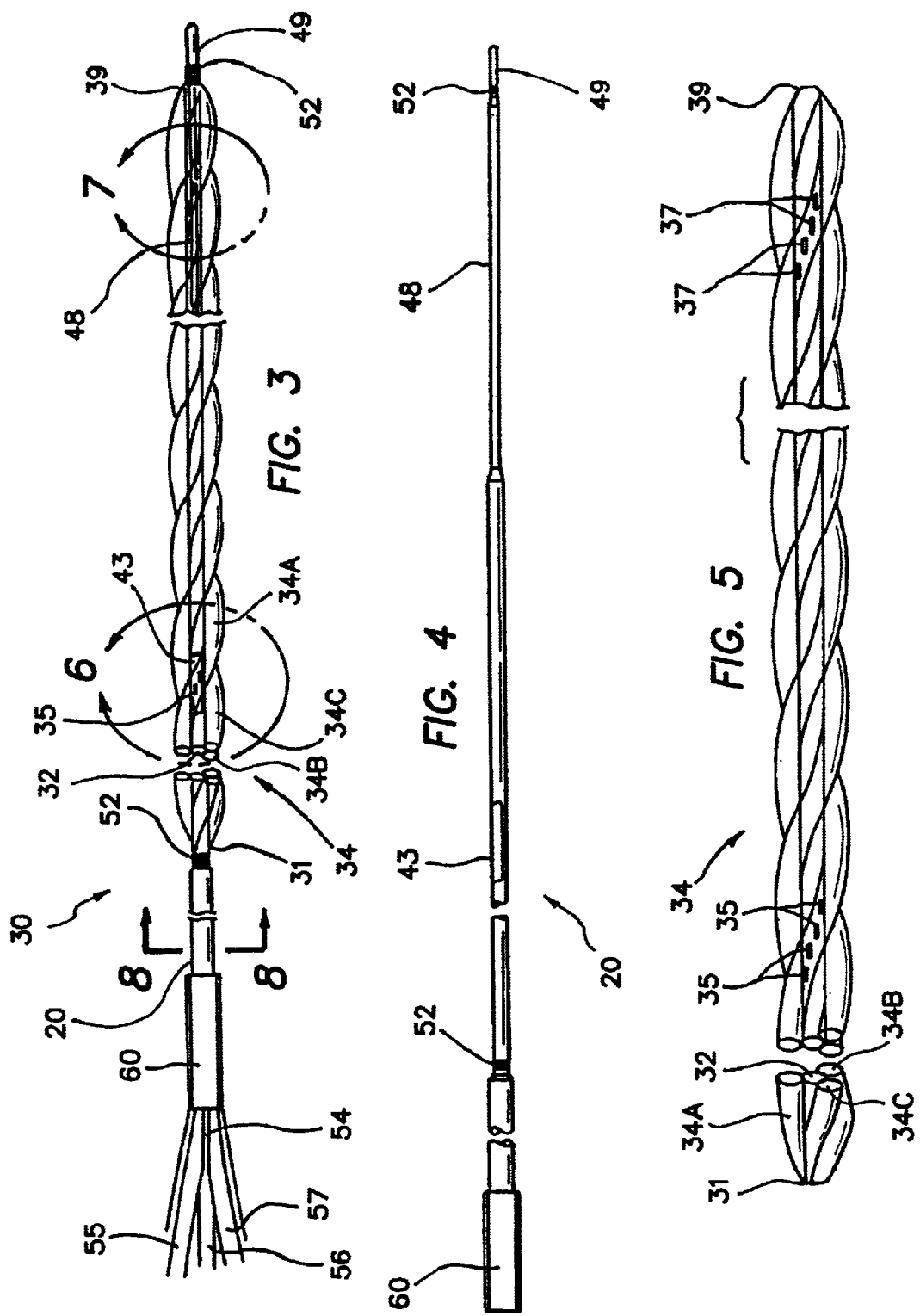

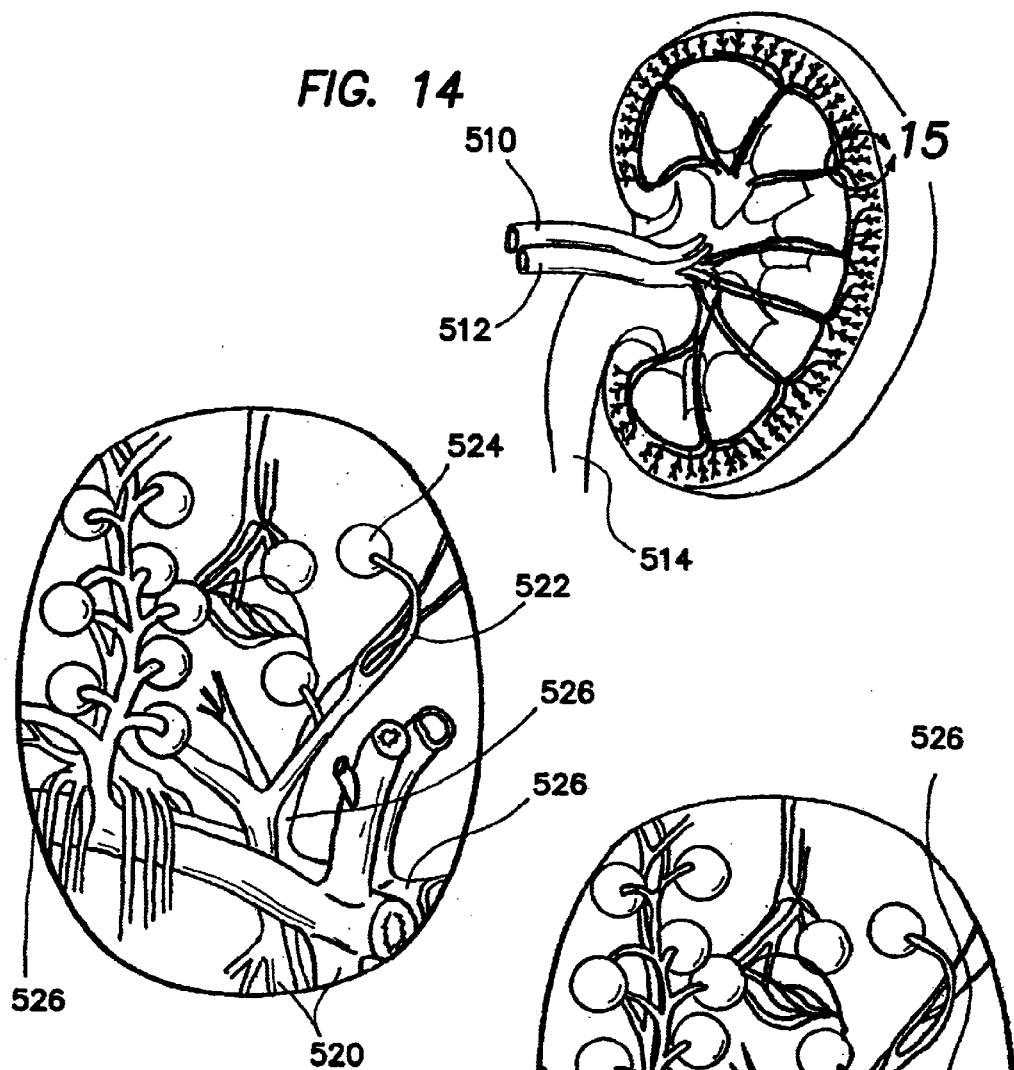
FIG. 14
FIG. 15
FIG. 16

METHODS AND SYSTEMS FOR REDUCING SUBSTANCE-INDUCED RENAL DAMAGE

FIELD OF THE INVENTION

This invention relates generally to medical devices and methods, and more particularly to systems and methods for avoiding or reducing substance-induced renal damage.

BACKGROUND OF THE INVENTION

Numerous drugs and other substances are known to be nephrotoxic. For example, radiographic contrast media (e.g., "contrast agent" or "dye"), non-steroidal antiinflamatory drugs (NSAID's), amphotericin, cisplatin, methotrexate, acyclovir, gentamicin, acetylcholinesterase inhibitiors, other nephrotoxic drugs, products of tumor lysis and products of rhabdomyolysis are known to cause damage to the kidneys.

In particular, radiologic contrast media (sometimes referred to as contrast agents or dyes) are frequently administered to patients undergoing radiographic investigations, such as fluoroscopy, X-ray, magnetic resonance and ultrasound imaging, to visualize blood vessels or blood flow and/or to enhance the image being obtained. For example, contrast medium may be administered to patients undergoing coronary angiography or other cardiac catheterization procedures. Delivery of the contrast media into a patient's vasculature enables the vasculature of different organs, tissue types, or body compartments to be more clearly observed or identified.

However, the use of radiographic contrast media may be associated with adverse side effects, including nephrotoxicity. In particular, contrast medium-induced nephrotoxicity is known to be an iatrogenic cause of acute renal failure in some patients. It has been reported that use of contrast media is the third most common cause of new onset renal failure in hospital patients. Patients who experience nephrotoxicity may experience changes in serum creatinine, or creatine clearance, at about one to five days after receiving the contrast medium. Consequences may be dramatic and can lead to irreversible renal damage and dialysis.

Acute deterioration in renal function is a recognized complication after coronary angiography, particularly for patients with pre-existing renal insufficiency. For patients with abnormal baseline renal function, the incidence of progressive renal deterioration may be as high as 42%. For hospitalized, critically ill patients, these results carry a poor prognosis for the patient, especially if dialysis becomes necessary. Factors that may predispose a patient for developing acute renal failure include, pre-existing renal insufficiency, diabetes mellitus, cardiovascular disease, including congestive heart failure, aging, and conditions characterized by depletion of effective circulatory volume.

Several mechanisms have been suggested for contrast medium-induced nephropathy. After radiographic contrast medium exposure, a brief period of vasodilation may be followed by renal vasoconstriction leading to intense reduction in renal blood flow, direct toxicity to renal tubular epithelium, tubular obstruction by protein precipitates, complement activation, and renal ischemia. In addition, patients at high risk of developing renal failure, including those with endothelial dysfunction, may not be able to dilate the renal vasculature, and thus experience a prolonged vasoconstrictive response. Vasoconstriction not only causes a decrease in renal blood flow and glomerular filtration rate, but it may also exacerbate medullary ischemia by decreasing oxygen supply since renal oxygen consumption is coupled to renal blood flow.

Attempts to reduce or prevent contrast medium-induced renal failure have included periprocedural hydration, forced diuresis, blood volume expansion, low osmolality versus high osmolality contrast agents, dopamine, calcium channel blockers, mannitol, atrial natriuretic peptide, acetylcholine esterase (ACE) inhibitors, the adenosine antagonist theophylline, endothelin receptor antagonists, and acetylcysteine. The attempts have generally been directed to reduce vasoconstriction and the negative effects that may be associated with vasoconstriction, such as the exacerbation of medullary ischemia. See, Renal Preservation Strategies for High Risk Patients, University of Chicago Prizker School of Medicine, (August 2000).

Mild hypothermia (e.g., approximately 32 degrees Celsius to approximately 36 degrees Celsius) has been shown to reduce metabolic requirements of organs, such as the heart and/or the brain. Indeed, if the hypothermia is systemic, the metabolic demands of the entire body may be reduced, so that the demands placed on the heart may be reduced. Hypothermia may also be effective to reduce ischemia in specific organs and to reduce the potential of organ damage due to such ischemia.

The physiology of hypothermia is fairly well understood. Normal human body temperature (approximately 37 degrees Celsius) may vary by approximately one degree Celsius. As body temperature decreases, resting muscle tone increases to attempt to generate heat, and the peripheral circulation is reduced to decrease blood flow to the skin to attempt to reduce heat loss. Shivering may develop as the body attempts to increase the metabolism and generate heat. When the temperature of the body decreases to approximately 35 degrees Celsius, shivering may be maximal. Below approximately 31 degrees Celsius, oxygen consumption may drop and shivering may cease. Patients with body temperatures below 27 degrees Celsius may be classified as severely hypothermic, and may be characterized by the cessation of voluntary movement, less than half normal cardiac output, and a significant risk of ventricular fibrillation.

One method for inducing hypothermia of a patient is through the use of a heat exchange catheter that is inserted into a blood vessel and used to cool blood flowing through that blood vessel. This method in general is described in U.S. Pat. No. 6,110,168 (Ginsburg), which is expressly incorporated herein by reference. Various heat exchange catheters useable for achieving the endovascular cooling are described in U.S. Pat. No. 5,486,208 (Ginsburg), PCT International Publication WO 00/10494 (Machold et al.), U.S. Pat. No. 6,264,679 (Keller et al.), PCT International Publication WO 01/58397, all of which are expressly incorporated herein by reference.

As indicated above, the potential for shivering is present whenever a patient is cooled below that patient's shivering threshold, which in humans is generally about 35.5° C. When inducing hypothermia below the shivering threshold, it is important to avoid or limit the shivering response in the patient. The avoidance or limiting of the shivering response may be particularly important in patients who suffer from compromised cardiac function and/or metabolic irregularities. An anti-shivering treatment may be administered to prevent or deter shivering. Examples of effective anti-shivering treatments are described in U.S. Pat. No. 6,231,594 (Dae et al.), the content of which is hereby incorporated by reference.

Thus, there remains a need in the art for improving patient outcome and organ preservation in patients that are administered contrast media, including patients who may be predisposed to developing acute renal failure induced by contrast media.

SUMMARY OF THE INVENTION

The present invention provides methods and systems wherein an endovascular heat exchange device is used to cool all or a portion of the body of a human or veterinary patient to prevent the occurrence of, or to reduce the severity of, renal damage that may result from blood-borne nephrotoxic substances, such as; radiographic contrast media (e.g., "contrast agent" or "dye"), non-steroidal antiinflamatory drugs (NSAID's), amphotericin, cisplatin, methotrexate, acyclovir, gentamicin, acetylcholinesterase inhibitiors, other nephrotoxic drugs, products of tumor lysis and products of rhabdomyolysis, etc. The method of the present invention is generally performed by inserting an endovascular heat exchange device into the vasculature of the patient and using such heat exchange device to cool all or a portion of the patient's body (e.g., at least the patient's kidneys) to a temperature at which the substance-induced renal damage is prevented or attenuated. The endovascular heat exchange device may be controlled by an automated controller that regulates the amount of heat exchanged by the heat exchanger to maintain the temperature of the renal parenchyma or kidney tissue (or the patient's core body temperature) within a temperature range that is optimal for reducing or avoiding the substance-induced renal damage.

In accordance with one specific embodiment of the invention, there is provided a method of reducing kidney damage resulting from administration of radiographic contrast medium to a human or veterinary patient. This method generally comprises the steps of a) positioning an endovascular heat exchange device in a blood vessel of the patient, and b) using the endovascular temperature exchange device to lower the temperature of the patient's body or at least the patient's kidneys to a temperature at which the nephrotoxic effect of the radiographic contrast medium is lessened or eliminated.

In accordance with other specific embodiments of the invention, there are provided methods for preventing or reducing the renal damage that occurs due to an overdose of a nephrotoxic drug (e.g., NSAID overdose), administration of a nephrotoxic drug to a patient whose kidney function is already impaired or other ingestion, absorption, formation or exposure of/to a nephrotoxic substance. This method generally comprises the steps of a) positioning an endovascular heat exchange device in a blood vessel of the patient, and b) using the endovascular temperature exchange device to lower the temperature of the patient's body or at least the patient's kidneys to a temperature at which the nephrotoxic effect of drug or other nephrotoxic substance is lessened or eliminated.

Still further in accordance with the invention, the endovascular heat exchange device may comprise a heat exchange catheter that is insertable into the vasculature of the patient. Such heat exchange catheter may have a discrete heat exchanger (e.g., a heat exchange region or heat exchange surface) that occupies less than the entire length of the catheter. The heat exchanger may be a flowing fluid type of heat exchanger wherein a thermal exchange fluid such as heated or cooled saline solution or water is circulated. In this regard, the heat exchange catheter may be in fluid communication with extracorporeal device(s) that control the temperature of and pump thermal exchange fluid (e.g., saline solution or water) through a heat exchanger located on the portion of the catheter that is positioned in the patient's vasculature. A programmable controller may be provided to control and maintain the temperature of all or a portion of the patient's body within a desired hypothermic, nephrotoxicity-reducing temperature range such as 32–36° C.

Still further in accordance with the invention, the foregoing methods may be practiced by positioning the endovascular heat exchange device in the blood vessel so that blood flows past or around the device, thereby cooling the blood that perfuses the patient's kidneys and, thus, cooling the kidneys themselves. The endovascular heat exchange device may comprises an inflatable balloon, either single lobed or multi-lobed, and/or may comprise a metallic surface capable of transferring heat. When inflatable balloons are utilized, the balloons may be inflated after being inserted into the patient. The balloons may be inflated by passing fluid, such as heat exchange fluid, through the lumens of the balloon, or may be inflated by passing gas through the balloon.

Still further in accordance with the invention, the foregoing methods may also include a step of disrupting the laminarity of blood flow around the endovascular heat exchange device. Such blood flow disruption may be caused by one or more flow disruptors (e.g., fins, projections, indentations, ridges, grooves, troughs, knobs, bumps, etc.) formed on or near the blood contacting surface of the endovascular heat exchange device. In addition, the flow disruption may be obtained by configuring the heat exchange device in a manner to alter the flow of blood around the device. For example, the lumens or lobes of a heat exchange balloon may be helically arranged around the shaft of a catheter.

The foregoing methods may also include a step of maintaining the reduced temperature for a sufficient time to reduce nephrotic side effects caused by the contrast medium. The patient's temperature may be reduced prior to the administration of the contrast medium, and may be maintained during and after the administration of the contrast medium.

The body temperature may be reduced to a temperature below 37 degrees Celsius, and in some instances, the patient's temperature will be reduced to between 32 degrees and 37 degrees Celsius. Because shivering may occur when the temperature of the patient is lowered, the methods may be practiced with a step of administering an anti-shivering mechanism to the patient. The anti-shivering mechanism may be a blanket, and/or it may be a pharmaceutical agent.

The foregoing methods may also include a step or steps of monitoring the patient's temperature, and adjusting the patient's temperature based on the monitored temperature.

In accordance with the disclosure herein, a medical system for reducing nephrotic injury induced by contrast medium that is administered to a patient may comprise an endovascular heat exchange catheter, and a temperature controller in communication with the catheter to cause a controlled temperature change of the heat exchange catheter that is sufficient to reduce the temperature of the patient's kidneys to reduce injury of the kidneys caused by the contrast medium. The heat exchange catheter may include a heat exchange balloon that receives heat exchange fluid from the temperature controller. The heat exchange balloon may be disposed about the catheter to direct the heat exchange fluid in an opposite direction of the blood flowing around the catheter. The temperature controller of the medical system may include temperature monitoring means and temperature adjusting means. The temperature monitoring means and the temperature adjusting means may be integrally provide with the controller, or may be separate components. The medical system may also include an anti-shivering mechanism that may be used to reduce shivering in the patient caused by the lowering of the patient's temperature.

Still further aspects and elements of the present invention will become apparent to those skilled in the art upon reading and considering the detailed descriptions of examples set forth herebelow and in the accompanying drawings.

BRIEF DESCRIPTION OF THE DRAWINGS

FIG. 1 depicts a patient with an endovascular heat exchange device positioned in the patient's vasculature with a heat exchange region in proximity of the patient's heart.

FIG. 2 is a cross-section along line 2—2 of FIG. 1.

FIG. 3 is a side view of a heat exchange region of a endovascular heat exchange device, which is a heat exchange catheter.

FIG. 4 is a side view of the shaft of the heat exchange catheter of FIG. 3.

FIG. 5 is a side view of the heat exchange region of the catheter of FIG. 3.

FIG. 14 is a sectional view of a patient's kidney with the renal artery, renal vein, and ureter depicted.

FIG. 15 is a magnified view along the section indicated in FIG. 14.

FIG. 16 is similar to FIG. 15 in which the patient's kidneys have been cooled.

DETAILED DESCRIPTION OF SPECIFIC EMBODIMENTS

The following detailed description is provided for the purpose of describing only certain embodiments or examples of the invention and is not intended to describe all possible embodiments and examples of the invention. For example, although the description herein describes an endovascular catheter device having a heat exchange region used to cool a patient to reduce contrast medium-induced nephropathy, the catheter device may be used to cool a patient to reduce injury to the kidneys caused by any agent or injury, or injury that may be exacerbated by normal or high metabolism. The cooling device may provide protection to the kidneys by reducing metabolic demands of the renal tissue and reducing the generation of agents, such as free radicals, that may contribute to cellular damage. In addition, although the catheter device of the invention is illustrated in position proximate to a patient's heart, the catheter device may be used near any organ or organs that may benefit from temperature control. For example, the device may be used in proximity to one or both kidneys to cool the kidneys in order to reduce injury to the kidneys. As will be apparent from the following disclosure, if the cooling device were to be positioned near the kidneys, it may be advantageous to position the device, or at least the heat exchange region of the device, within a renal artery to provide more direct cooling to the renal vasculature.

Figure 17:
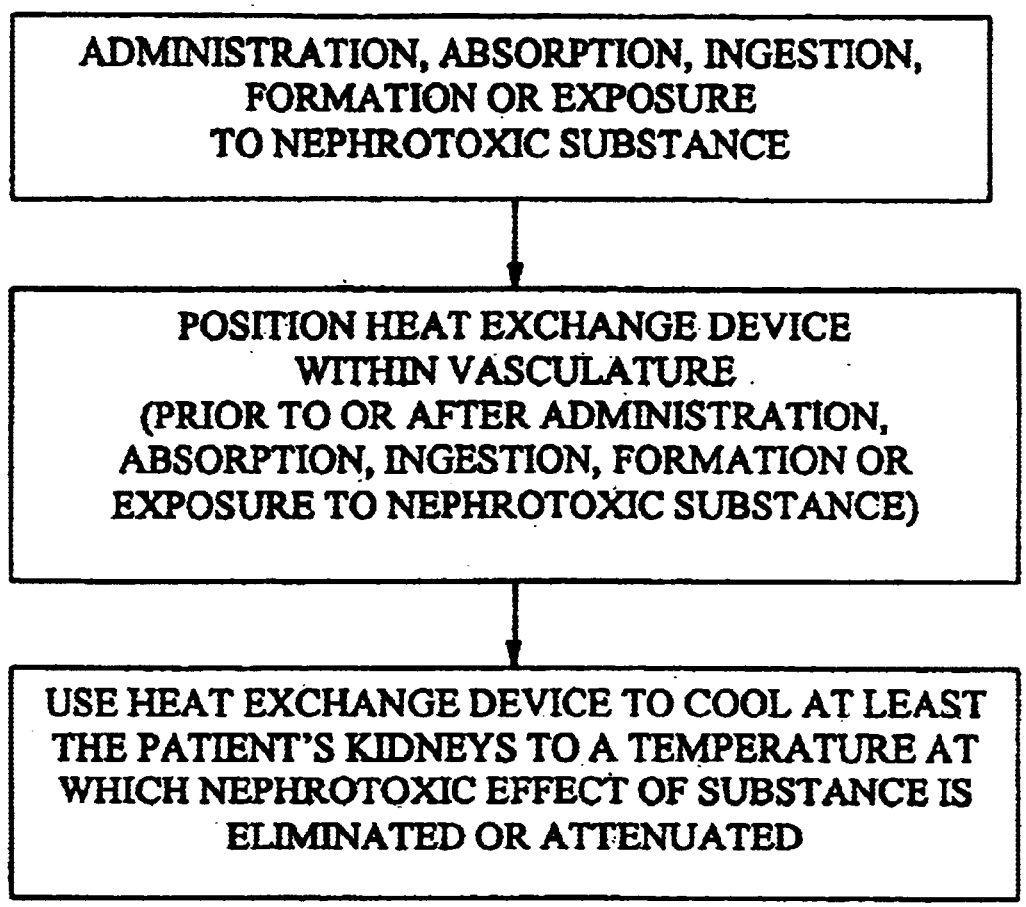
FIG. 17 is a flow diagram of a general method for reducing substance induced nephrotoxicity in accordance with this invention.
Figure 18:
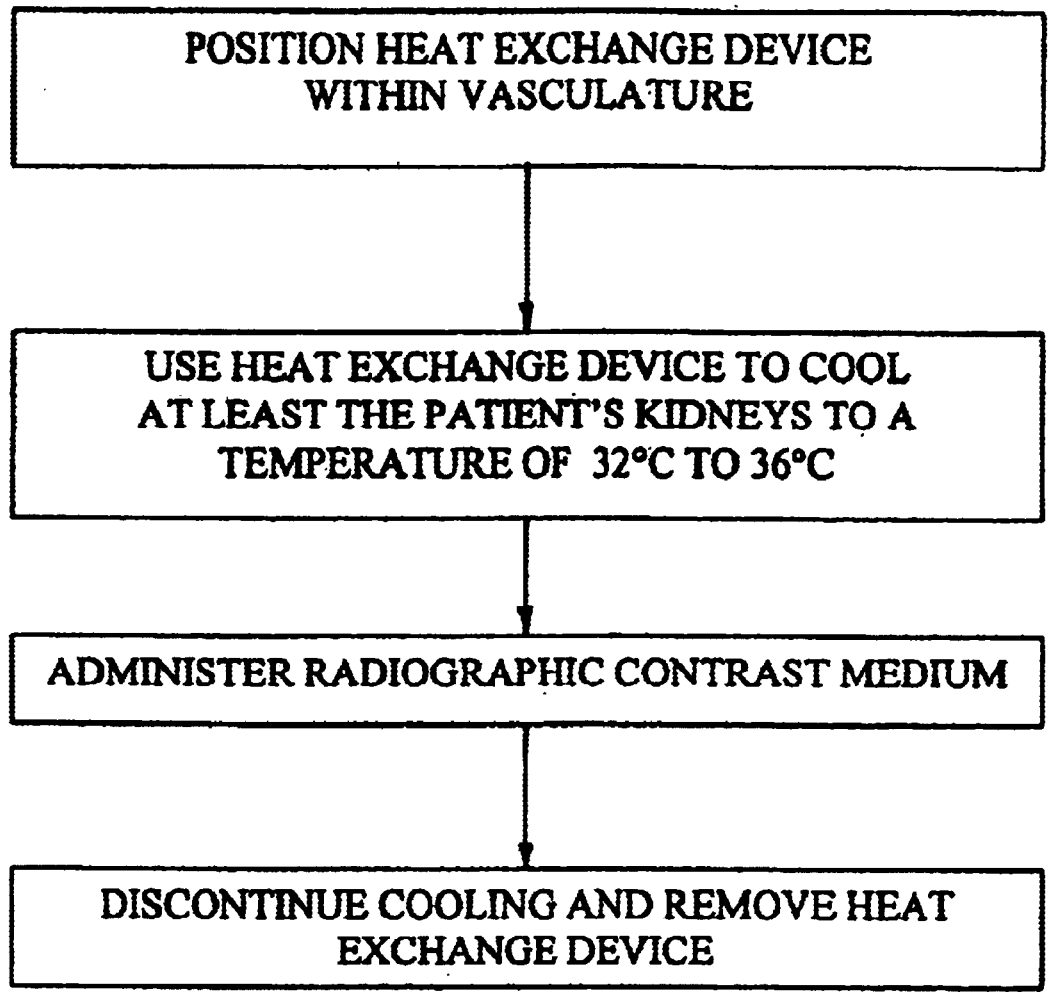
FIG. 18 is a flow diagram showing one example of a method for preventing or reducing the severity of the nephrotoxicity that may result from the administration of radiographic contrast medium to a patient who already suffers from impaired renal function.

Referring to the figures, and in particular, FIGS. 1, 17 and 18, an endovascular heat exchange catheter device, which comprises a heat exchange surface or region 30, is positioned in a patient's vascular system. Endovascular heat exchange catheter device has a heat exchange region 30 that causes a change in temperature of the blood flowing around the heat exchange region. As illustrated in FIG. 1, endovascular heat exchange catheter device is an endovascular catheter that has been inserted through a person's femoral vein FV and inferior vena cava IVC so that the distal end of the catheter device (e.g., the heat exchange region) is positioned near or in the right atrium RA of the heart H. Heat exchange region 30 is capable of being heated or cooled to cause heating or cooling of the patient. Heat exchange region 30 is selectably adjustable to provide a desired change in the patient's temperature. The temperature of the patient may be controlled by changing the temperature of heat exchange region 30 so that blood flowing around heat exchange region 30 is either cooled, warmed, or kept at a desired temperature. As shown in FIG. 1, heat exchange region 30 is positioned proximate the patient's heart so that the blood entering the right atrium of the patient's heart has been exposed to the heat exchange region 30 and has experienced a change in temperature by flowing around heat exchange region 30. Accordingly, heat exchange region may be positioned in the IVC, the superior vena cava (SVC), or it may be positioned in both the IVC and SVC.

Because essentially all of a patient's blood enters the heart via the inferior and superior vena cava, cooling of blood flowing through either the inferior or superior vena cava is an effective way to cool the patient's heart as well as the patient's entire body. In addition, when the blood entering the right atrium of the heart is cooled, the temperature of the body core other than the cardiac muscle may lag the hypothermia experienced by the cardiac muscle, which may result in relatively less hypothermia than that experienced by the cardiac muscle. Accordingly, when attempting to cool the patient's kidneys to reduce renal injury, it may be necessary to decrease the temperature of the blood flowing around heat exchange region to a greater degree than if the heat exchange region was being used to primarily cool the heart. The greater decrease in temperature may be provided by lowering the temperature of the heat exchange region, or cooling the patient for long periods of time, such as for two or more hours. For example, it may be desirable to decrease the temperature of the heat exchange region to 30 degrees Celsius to cause the temperature of the kidneys to decrease to 32 degrees Celsius. In addition, affective kidney cooling may also be provided by positioning the heat exchange region in a blood vessel in closer proximity to the kidneys than the heart. For example, and as indicated above, heat exchange region could be positioned in the abdominal aorta just superior to the renal arteries or separate heat exchange surfaces or regions 30 may be placed in each renal artery to provide more direct and local cooling of the kidneys.

In some applications, local or selective cooling of the renal parenchyma or the associated region of the body may be desirable. This may be accomplished by accomplished by positioning first heat exchange surface(s) or region(s) 30 within the abdominal aorta just superior to the renal arteries or in the renal arteries themselves and positioning second heat exchange surface(s) or region(s) 30 within the abdominal aorta just inferior to the renal arteries and/or elsewhere within the body (e.g., within the venous vasculature such as within the inferior vena cava superior to the renal veins). The first heat exchange surface(s) or region(s) 30 are used to cool blood flowing to the kidneys and the second heat exchange surface(s) or region(s) 30 are used to rewarm blood that has exited the kidneys.

It may also be desirable to provide relatively greater cooling of the kidneys without providing a similar amount of cooling to the heart, for example, it may be desirable to cool the kidneys to 32 degrees Celsius and cool the heart to 36 degrees Celsius. In such instances, a heat exchange region of an endovascular heat exchange device may be positioned in the renal vasculature, such as a renal artery, and another heat exchange region of another endovascular heat exchange device may be positioned in proximity of the heart, such as in the vena cava, to provide a local temperature control of the heart and the organs in proximity of the heat exchange region. It may also be possible to provide two or more heat exchange regions with a single endovascular heat exchange device so long as the endovascular heat exchange device is structured to permit the independent temperature control of each heat exchange region. Thus, by way of example, it may be possible to locally cool the patient's kidneys to one temperature, such as 32 degrees Celsius, and to keep the heart, and perhaps the rest of the body at a relatively warmer temperature, such as 36 degrees Celsius.

The endovascular heat exchange catheter device shown in FIG. 1 is an endovascular catheter device having one heat exchange balloon at the heat exchange region 30. However, other types of endovascular heat exchange devices could be utilized to provide temperature adjustments to patients without departing from the scope of the invention. For example, an endovascular heat exchange device may have a plurality of heat exchange balloons at the heat exchange region, or an endovascular heat exchange device may have a metallic heat exchange region. Such a device would be capable of transmitting energy to the metallic heat exchange region such that the temperature of the metal changes and causes a change in the temperature of the blood flowing therearound. The temperature of the heat exchange region may increase or decrease as desired to cause a desired and selective cooling of the patient, including the patient's kidneys.

In addition to heat exchange region 30, endovascular catheter device 10 comprises a catheter shaft 20. Catheter shaft 20 may be a tube having a proximal end, a distal end, and one or more lumens extending from the proximal end towards the distal end, as described herein. At least one of the lumens of catheter shaft should extend the length of the catheter device. In the embodiment illustrated in FIG. 1, heat exchanger 30 is positioned at the distal end of catheter device 10.

Catheter device 10 may be connected to a control system 100. Control system 100 may be one apparatus, or a plurality of apparatus. As illustrated, control system 100 comprises a temperature regulator, or external heat exchanger, 110 to control the delivery and return of heat exchange fluid that may flow the lumens of the catheter device 10. Control system 100 may also comprise a control unit 120 for controlling the flow of heat exchange fluid through temperature regulator 110. Control unit 120 may also be operably connected to an electrocardiogram (ECG) monitoring apparatus 130, and/or to a temperature monitoring apparatus 140. The ECG monitoring apparatus may monitor an ECG signal 132 from the patient and may provide an ECG signal 134 to control unit 120, and the temperature monitoring apparatus 140 may measure a temperature signal 142 and provide a temperature signal 144 to control unit 120. In one embodiment, various sensors may be placed on or in the patient to sense various parameters of the patient and generate a signal that is carried to the controller to allow the controller to control the function of the catheter device based on those parameters. For example, a temperature sensor 146 may be placed in the patient, for example in the femoral vein contra-lateral to the location of the catheter device, to sense the core temperature of the patient and provide a temperature signal 142 of the patient by a connection to the temperature monitoring device and/or controller. In response to this information, the controller may alter the temperature of the heat exchange fluid to increase the patient's temperature, decrease the patient's temperature, or maintain the patient's temperature. In addition, or alternatively, the controller may alter the flow rate of the heat exchange fluid to cause an increase or decrease of the patient's blood temperature.

FIG. 2 is a sectional view along line 2—2 of FIG. 1. As illustrated, and in one embodiment, catheter shaft 20 comprises a plurality of internal lumens permitting the flow of fluid, such as a gas or liquid, through the lumens to and from the heat exchange region 30. For example, catheter shaft may comprise a heat exchange inflow lumen 22A and a heat exchange fluid outflow lumen 22B, and a working lumen 24 that may be used for a guide wire or the administration of medicaments from the proximal end of the catheter through the distal end of the catheter. Although catheter shaft 20 is illustrated as having three lumens, as one skilled in the art will recognize, depending on the configuration of the heat exchange region and/or additional components provided on catheter device 10, various configurations of catheter shaft 20 might be appropriate. For example, additional lumens may be provided to permit the flow of one or more additional fluids, for example, oxygen or an oxygenated or superoxygenated liquid, which may be useful to oxygenate the blood flowing around the catheter device. One or more additional lumens may also be provided to contain one or more probes or sensors, which may be used to monitor one or more conditions of the patient, for example, temperature or blood oxygen content. As discussed elsewhere herein, such probes or sensors may additionally or alternatively be provided as separate elements from the catheter device. In addition, although the illustrated embodiment depicts three lumens within a single tubular structure, other embodiments may include three tubes that are secured together to act as the structure depicted. Similarly, any number of tubes may be utilized depending on the particular heat exchange region being employed and the treatment being administered.

FIG. 3 illustrates a view of heat exchange region 30 of a endovascular heat exchange device. As shown in FIG. 3, heat exchange region 30 comprises a multi-lobed balloon having a plurality of outer lumens 34, and in particular, three helically arranged outer lumens 34A, 34B, and 34C. The outer lumens are helically arranged around a central lumen 32. The four-lumen balloon is disposed over an inner shaft 40 (see FIG. 4), in particular, inner shaft 40 extends through central lumen 32. The lumens of the multip-lobed balloon are attached to shaft 40 at the balloon's proximal end 31 and the balloon's distal end 39. The lumens may be attached in any suitable manner that provides an airtight or liquid tight seal to reduce leakage of fluid from the lumens of the balloon. For example, an adhesive, such as an adhesive that cures upon exposure to UV light, may be applied around the ends of the balloon to create a fluid tight seal. In addition, a radiopaque band or marker, such as a gold or platinum band, may be provided near the heat exchange region 30 to permit radiographic visualization of the heat exchange region during the course of the procedure. As illustrated, a radiopaque band 52 is provided at the proximal and distal ends of heat exchange region 30.

Although the heat exchange balloon is illustrated in FIG. 3 as having three helically arranged outer lumens disposed around an internal lumen, in other embodiments, heat exchange lumens 34A, 34B, and 34C could be arranged linearly, e.g., the lumens may be disposed around inner lumen 32 and parallel to the length of catheter shaft 40, or heat exchange lumens could be arranged around inner lumen 32 and orthogonal to the length of the shaft. The lumens 34 may be made of any suitable material that is flexible and elastic, and that provides sufficient heat transfer properties to cause changes in the temperature of a patient's bloodstream. One example of a suitable lumen material includes polyethylene terephthalate (PET).

Heat exchange region 30 of the catheter device of the invention may be expandable such that the outer lumen or lumens 34 may be expanded and contracted. The expandable nature of the heat exchange region 30 facilitates insertion of the catheter device 10 into a patient's vascular system, and improves the heat exchange capabilities of the catheter device. For example, contracting the heat exchange region reduces the cross-sectional size of the heat exchange region so that it can be inserted into a vein or the like without risking damaging the vein, or the catheter device. In addition, expanding the heat exchange region will increase the surface area of the heat exchange region so that more blood is exposed to the heat exchange surface and the temperature of the blood may be efficiently controlled. Examples of endovascular heat exchangers include those disclosed in PCT publications WO 01/13809 and WO 01/58397, the contents of which are hereby incorporated by reference.

Figure 6:
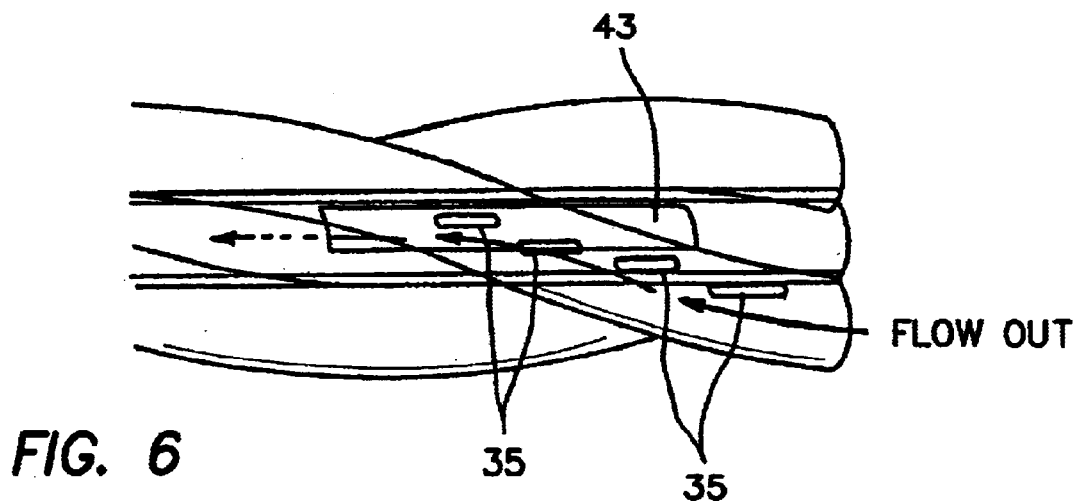
FIG. 6 is an enlarged view of section 6 of the device of FIG. 3.
Figure 7:
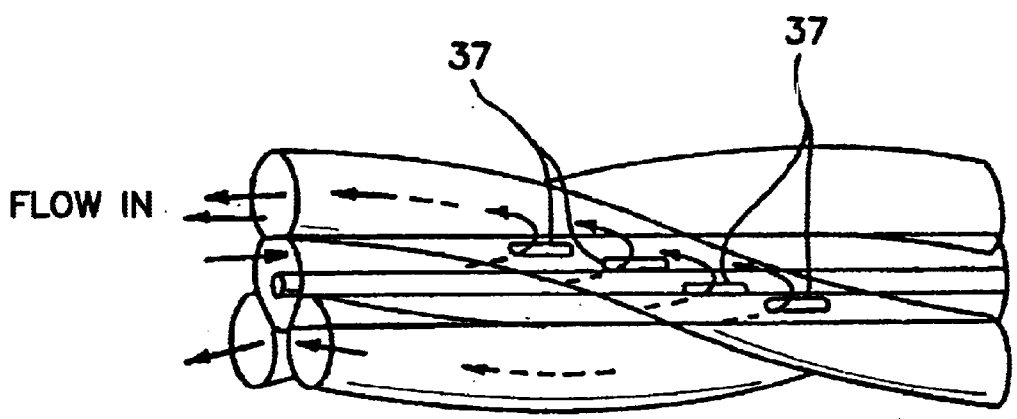
FIG. 7 is an enlarged view of section 7 of the device of FIG. 3.
Figure 8:
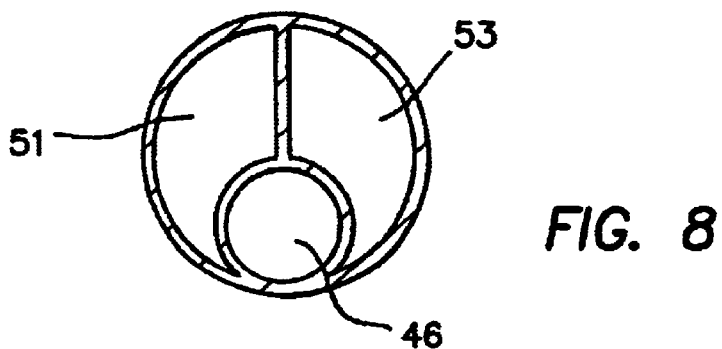
FIG. 8 is a section view along line 8—8 of FIG. 3.

The lumens 34 of heat exchange region 30 are in communication with ports 55 and 57 of hub 54. A guide wire port 56 may also be provided to direct a guide wire through a guide wire lumen disposed within heat exchange region 30. When heat exchange fluid is utilized to alter the temperature of the heat exchange device, ports 55 and 57 are in fluid communication with the lumens 34 of heat exchange region 30 so that fluid may flow through inflow port 55 through lumen 32 towards the distal end 39 of heat exchange region 30, and proximally through outer lumens 34A, 34B, and 34C to outflow port 57. This directional flow provides efficient rates of heat exchange between heat exchange region 30 and the patient's blood because the heat exchange fluid is flowing in an opposite direction from the flow of the patient's blood. As used herein, the opposite flow of the heat exchange fluid is referred to as counter-current flow. In the illustrated embodiment, and by way of example and not by way of limitation, heat exchange fluid may flow through inflow port 55 into an inflow lumen 51 of inner shaft 40 (see FIG. 8) to the distal end 39 of heat exchange region 30 where the fluid may then flow through one or more apertures 37 (FIGS. 5 and 7) into outer lumens 34A, 34B, and 34C. The heat exchange fluid then flows proximally (i.e., towards the proximal end of the heat exchange catheter) toward one or more apertures 35 provided in inner lumen 32 (FIGS. 3, 5, and 6) and then flows into a window 43 provided in inner shaft 20 and through outflow lumen 53 so that the fluid may flow through outflow lumen 53 (FIG. 8). One example of a heat exchange fluid is saline; however, other fluids may also be used in accordance with the invention. In other embodiments of the invention, the heat exchanger may comprise a thermoelectric element or a chemically cooled member mounted within or on the catheter body and operably connected to control system 100. When employing an endovascular heat exchange device that does not have inner lumens, such as a device with a metallic heat exchange region, the metallic heat exchange region can experience a temperature change that is greater at the distal end of the heat exchange region and reduces toward the proximal end of the heat exchange region.

As persons skilled in the art will appreciate, the particular flow pattern may be adjusted from that described above depending on, among other things, the position of the heat exchange region within the patient's vasculature. For example, if the heat exchange region were to be positioned in a blood vessel where the blood flow proceeds from the distal end of the heat exchange region towards the proximal end, it may be advantageous to cause the heat exchange fluid to flow into lumens 34A, 34B, and 34C at the proximal end, and to flow into inner lumen 32 at the distal end. Other configurations are also conceivable to those skilled in the art so long as the heat exchange region causes a desired temperature change in the blood flowing therearound.

A flexible length of tube 49 may be joined onto the distal end of the guide wire tube to provide a flexible tip to the catheter. Alternatively, a soft tip may be attached over the very distal end of the catheter. The distal end of the flexible tube 49 is open so that a guide wire may exit the tip, or medicine or radiographic fluid may be injected distal of the catheter through the guide wire lumen.

Figure 9:
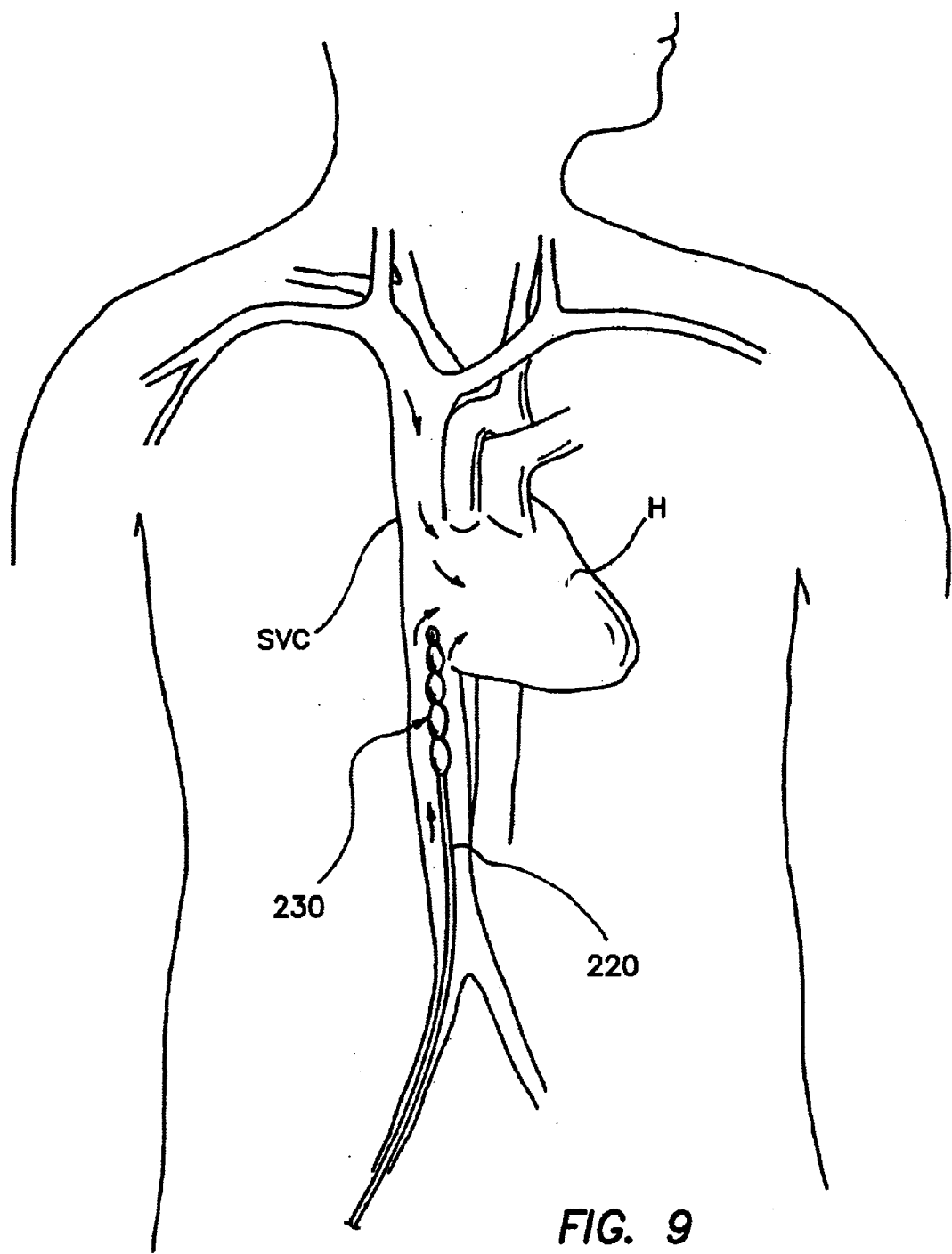
FIG. 9 illustrates a spiral shaped heat exchange region on a endovascular heat exchange device.
Figure 10:
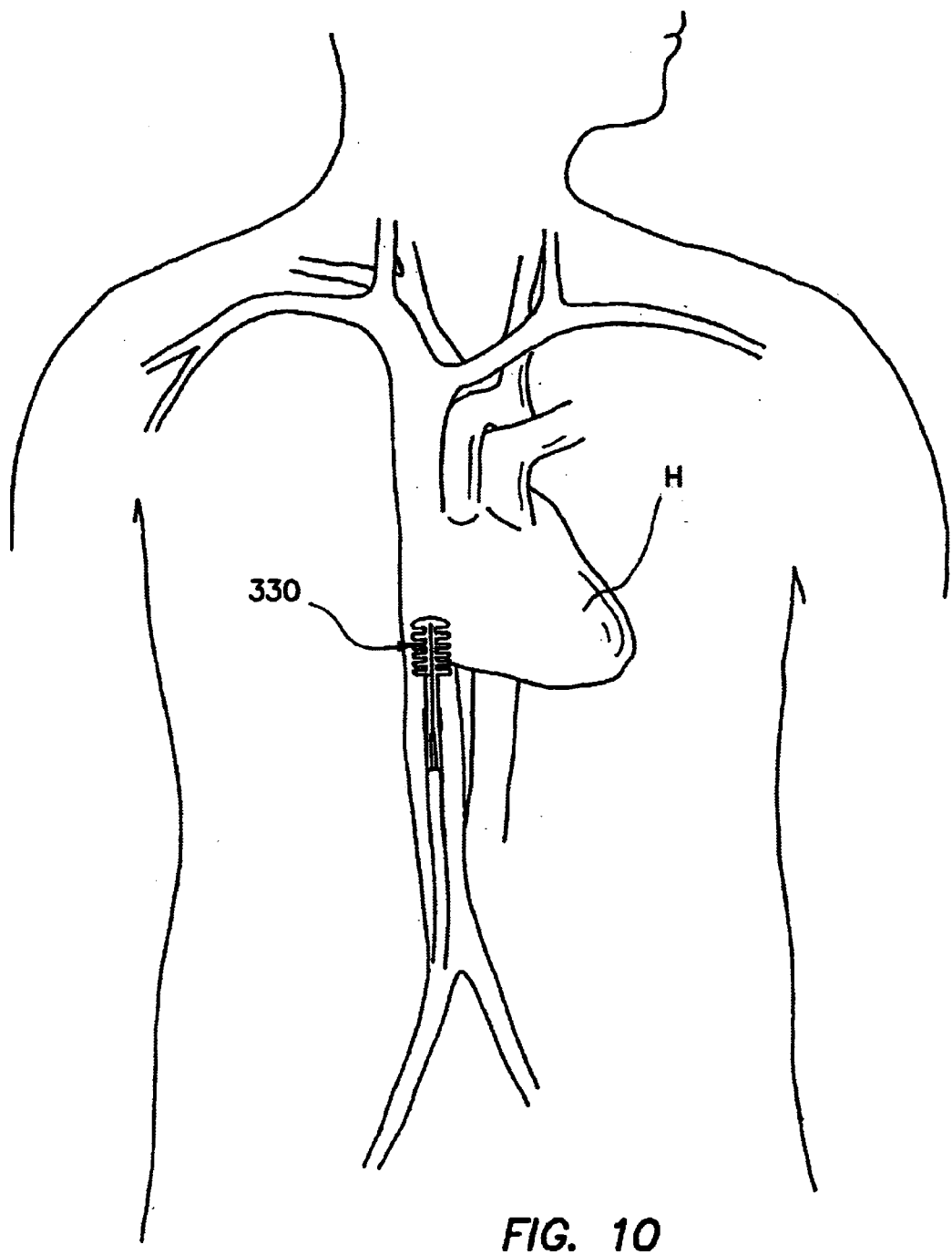
FIG. 10 illustrates a heat exchange region of an endovascular heat exchange device with a plurality of disks.
Figure 11:
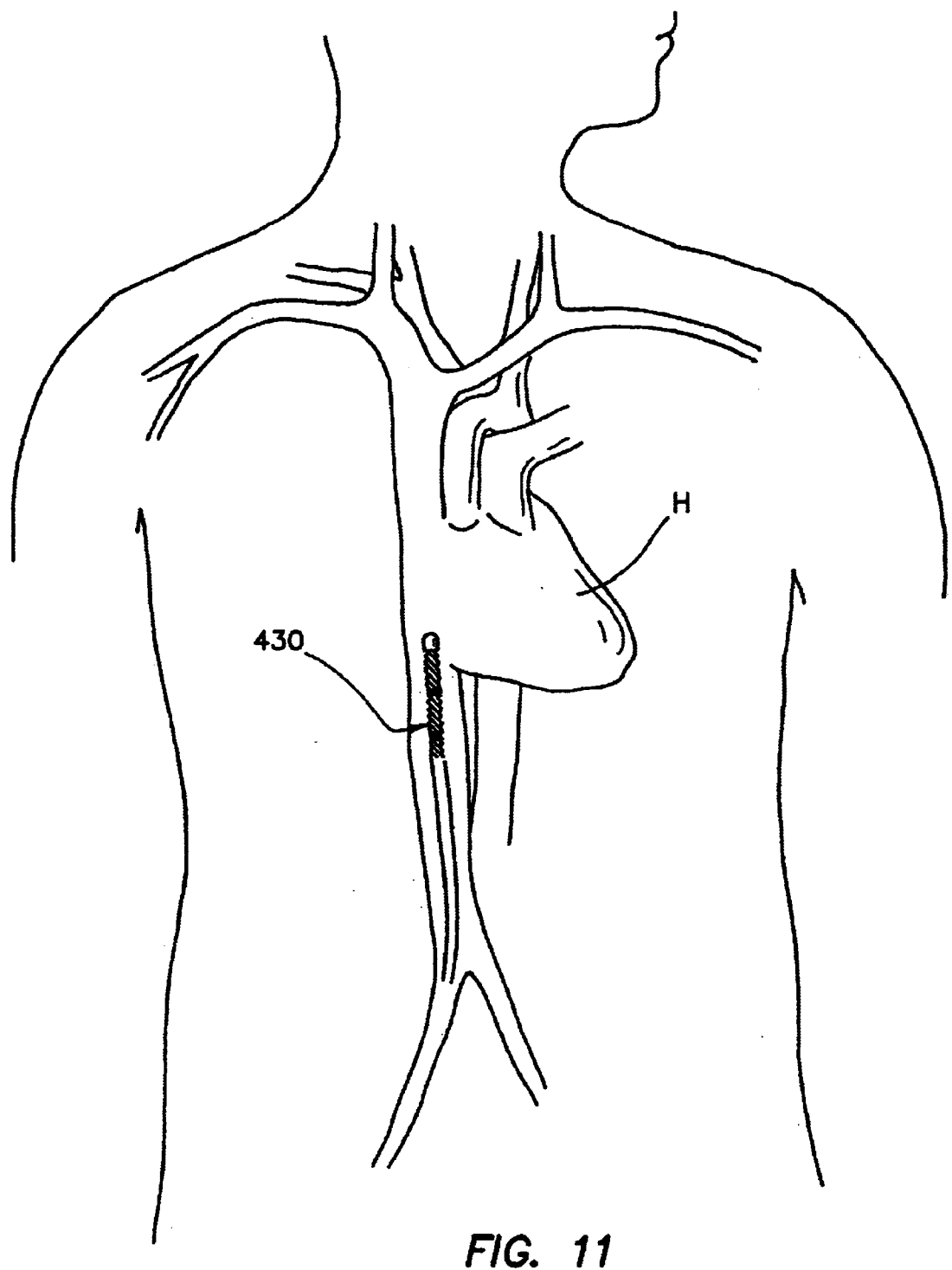
FIG. 11 illustrates a heat exchange region that is metallic and includes a plurality of fins.
Figure 12:
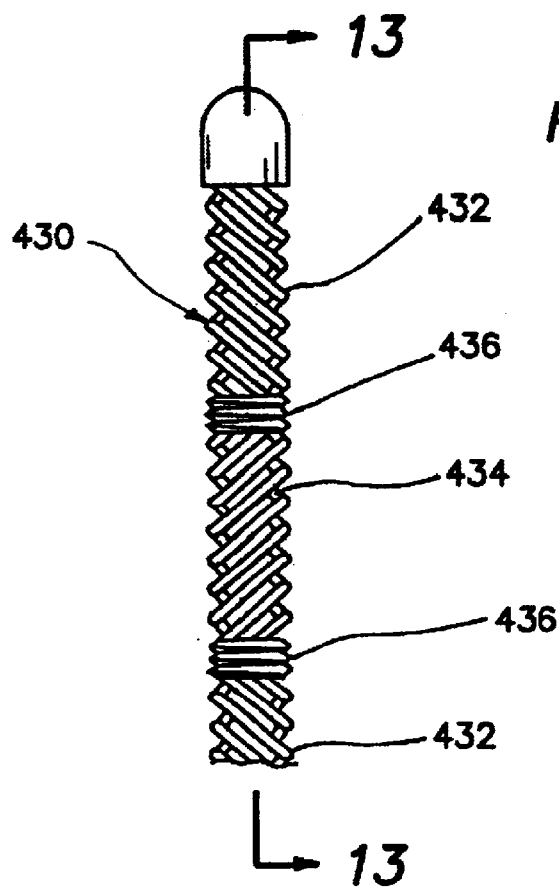
FIG. 12 is a view of the heat exchange region of FIG. 11.
Figure 13:
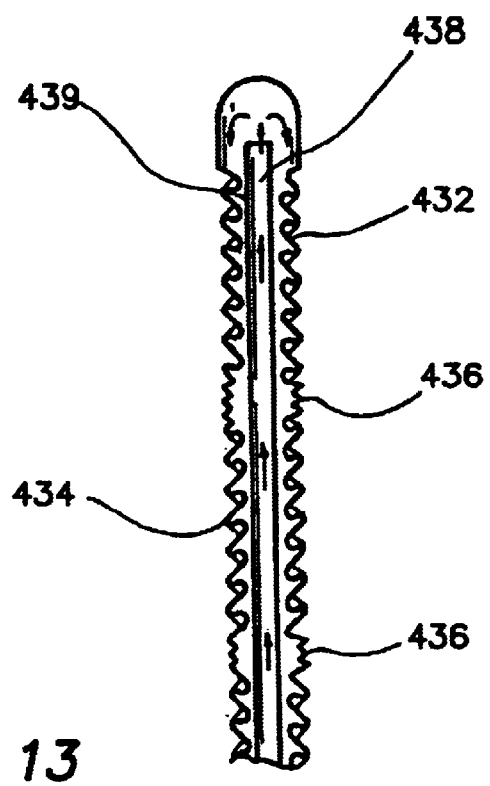
FIG. 13 is a sectional view along line 13—13 of FIG. 12.

In addition, the catheter device disclosed herein may include one or more flow disruption devices to disrupt the laminarity of blood flow around the catheter device. As understood by persons skilled in the art, blood may flow around the catheter device and may become laminarly organized so that certain streams or lamina will contact the catheter device, but other lamina will not. Thus, disrupting the laminar flow of blood around the catheter device increases the probability that more blood will be exposed to the catheter device, and therefore, more blood will experience a temperature change. Any type of flow disruption device may be used in accordance with the present invention. For example, one or more ribs may be provided on the exterior of the catheter shaft or the heat exchange region. In addition, the heat exchange region may be structured so that it is spiral shaped as illustrated by heat exchange region 230 of FIG. 9. The helical shape may increase heat exchange surface area and, in some embodiments, may additionally serve to disrupt the laminarity of blood flow adjacent to the heat exchange surface especially in embodiments where motion (e.g., vibration, shaking, twisting or back and forth longitudinal movement) is imparted to the heat exchange region. FIG. 10 illustrates a heat exchange region 330, which comprises a plurality of flexible disks. The flexible disks may be inflatable to achieve at least some of the advantages provided by an expandable multi-lobed balloon. FIG. 11 depicts a metallic heat exchange region 430. A view of heat exchange region 430 is shown in FIG. 12. Heat exchange region 430 may have fins (i.e., surface projections, ridges, corrugations and the like) disposed on its outer surface. For example, heat exchange region 430 is shown as having multiple segments of left-handed helical fins 432, a segment of right-handed helical fins 434, and bellows-shaped or corrugation-like fins 436. A longitudinal sectional view along line 13—13 of heat exchange region 430 is shown in FIG. 13. As shown, heat exchange region 430 may comprise an internal lumen 438 to direct a heat exchange fluid toward the distal end of heat exchange region 430, and an outer lumen 439 to direct the heat exchange fluid in a counter-current direction toward the catheter shaft of the catheter device. Another example of a flow disruption device may be a pulsatile balloon disposed along the catheter shaft of the endovascular heat exchange device.

The catheter device of the invention may be inserted into a patient's vascular system. As described hereinabove, the catheter device is advanced within the patient so that the heat exchange region is in proximity to the heart or kidney to affectively cool the kidneys. The position of the catheter device may be monitored during the procedure by monitoring the position of the guide wire, or the radiopaque markers provided on the device, using conventional imaging means. When the catheter device is in a desired position, heat exchange fluid may be directed or urged through the heat exchange region to cause a temperature change in the patient's blood, which causes a corresponding change in the temperature of the renal tissue. Thus, the catheter device may be used to control the patient's temperature, and in particular, the temperature of the patient's kidneys.

In accordance with the invention herein disclosed, kidney damage in a patient that is administered radiographic contrast medium or another nephrotoxic substance may be reduced by positioning the adjustable endovascular heat exchange device within a blood vessel of the patient, and adjusting the temperature of the endovascular heat exchange device to cause a reduction in the patient's temperature that is sufficient to reduce the temperature of the patient's kidneys. The kidneys are cooled so that the metabolic requirements of the renal tissue are reduced, and thus, the oxygen requirements are reduced. Without wishing to limit the invention to any particular theory or mechanism of operation, it is believed that despite the vasoconstriction (e.g., the constriction of the blood vessels) induced by the cooling of the patient, the reduction in renal metabolism is sufficient to reduce damage induced by the administered contrast media. Accordingly, the cooling of the patient results in reduced contrast medium-induced nephrotoxicity and reduced acute renal failure caused by the nephrotoxicity. FIGS. 14 to 16 illustrate an example of the vasoconstriction induced by the temperature reduction of the endovascular endovascular heat exchange device. FIG. 14 is a sectional view of a kidney depicting the renal artery 510 and the renal vein 512, and the ureter 514. FIG. 15 is a magnified view along line 15 of FIG. 14. Interlobar arteries 520 are depicted as branching into vas afferens 522 and projecting to renal corpuscle 524. Renal corpuscle 524 includes Bowman's Capsule and the glomerulus, and is the primary site of blood filtration. The renal venous system is depicted by 526. FIG. 16 depicts the renal vasculature after the cooling caused by the endovascular heat exchange device. The temperature reduction causes the renal arteries 520 and renal veins 526 to constrict so that the blood flow is reduced through the renal vasculature. As discussed herein above, vasoconstriction that may result from the administration of contrast media is believed to contribute to contrast medium-induced nephrotoxicity. However, it has been discovered that by reducing renal metabolism by reducing the patient's temperature in connection with administration of contrast medium, the vasoconstrictive effects are not as harmful, and renal damage may be reduced or prevented.

Contrast media are well known in the art, and any conventional contrast media may be used at the discretion of the attending physician. Contrast media may include, and are not limited to, iodinated contrast agents, high osmolality contrast agents, low osmolality contrast agents, and biodegradable contrast agents. Some examples of contrast media are disclosed in U.S. Pat. Nos. 5,993,780 and 6,265,610, the contents of which are hereby incorporated by reference.

Other types of substances are also known to be nephrotoxic, including radiographic contrast media (e.g., "contrast agent" or "dye"), non-steroidal anti-inflammatory drugs (NSAID's), amphotericin, cisplatin, methotrexate, acyclovir, gentamicin, acetylcholinesterase inhibitiors, other nephrotoxic drugs, and internally generated substances such as products of tumor lysis and products of rhabdomyolysis and toxins associated with infections or septicemia, and the methods of the present invention may also be used to prevent or mitigate renal damage due to an overdose or other ingestion, absorption or exposure to such nephrotoxic substances.

In certain embodiments of the invention, the patient's temperature is reduced before the contrast medium or other nephrotoxic substance is administered to the patient. Accordingly, the metabolism of the renal tissue will be reduced prior to the administration of the contrast medium. In other embodiments, the patient's temperature is reduced during or after the administration of contrast medium or other nephrotoxic substance to the patient. The reduced temperature may be maintained for a length of time to reduce the renal ischemic effects caused by the contrast media. For example, the reduced temperature may be maintained during the administration of the contrast medium. The temperature of the patient is reduced below 37 degrees Celsius, and in certain embodiments, the temperature of the patient is reduced to a temperature between 32 degrees and 37 degrees Celsius.

As indicated above, the cooling of the patient's body may cause some shivering to occur, if the patient's core body temperature is cooled to less than about 35.5° C. In such cases, it may be desirable to administer an anti-shivering mechanism to prevent or lessen the shivering and enhance the patient's comfort. An anti-shivering mechanism may comprise the application of warmth to the patient's skin as may be accomplished by a warming blanket of the type commonly used in hospitals. Alternatively or additionally, an anti-shivering mechanism may comprise the administration of drugs or agents to minimize or prevent the shivering response. Examples of agents that are useable for this purpose are described in U.S. Pat. No. 6,231,594 (Dae et al.), which is incorporated herein by reference. For example, an anti-shivering mechanism may comprise the steps of:

(i) warming the skin;
(ii) administering an initial bolus dose of a first anti-thermoregulatory response agent to the patient (for example an oral dose of a serotonin 5 HT1a receptor agonist such as 60 mg of buspirone);
(iii) administering a subsequent dose of a second anti-thermoregulatory response agent to the patient (for example an initial intravenous dose of an opioid receptor agonist such as 50 mg of meperidine administered by slow push followed by a similar second dose); and
(iv) administering a further dose of the second anti-thermoregulatory response agent by constant IV administration (for example, constant IV administration of about 25 mg/hr of meperidine).

Alternatively, another anti-shivering treatment that may be more suitable for longer term use (e.g., more than 24 hours) comprises the following steps:

(i) administering a first dose of an anti-thermoregulatory response agent to the patient (for example an intravenous dose of an opioid receptor agonist such as 50 mg of meperidine administered by slow push and infused over about 5 minutes);

(ii) administering a second dose of the anti-thermoregulatory response agent to the patient (for example, about 15 minutes after the initial administration of meperidine, an additional 50 mg of meperidine is administered by slow IV push);

(iii) administering a third dose of the anti-thermoregulatory response agent by constant IV administration (for example, constant IV administration of about 25 mg/hr of meperidine maintained for the duration of the time that the patient's temperature is below the shivering threshold);

(iv) an intravenous temperature control catheter of the general type described above is introduced into the vasculature of the patient and the heat exchange region of the catheter is placed in the IVC and cooling is begun at the maximum rate. The patient is thereafter maintained at a therapeutically low temperature even below the shivering threshold.

Another class of anti-shivering drugs that may be particularly useful are the alpha-adrenergic receptor agonists, such as dexmedetomidine and clonidine, dopamine receptor blockers; dopamine receptor agonists; kappa opioid receptor agonists; opioid agonist-antagonist analgesics; and their pharmaceutically acceptable salts.

In practicing the foregoing methods, any of the endovascular heat exchange devices disclosed herein above may be utilized to achieve the desired temperature regulation of the patient. The endovascular heat exchange device should be insertable into a blood vessel of the patient without blocking blood from flowing around the device. Thus, and as described herein, the patient's temperature can be adjusted and controlled as needed by adjusting the temperature of the endovascular heat exchange device to cause a change in the temperature of the blood flowing around the device.

In addition, the methods of the invention may include one or more steps of administering cellular protective agents, such as agents that reduce or prevent, cellular death (apoptosis) resulting from injury. Protective agents may include, but are not limited to, anti-excitotoxic agents, such as glutamate receptor modulators, gamma-aminobutyric acid (GABA) receptor modulators, ion channel modulators, such as calcium channel blockers, and free radical scavengers.

Although several illustrative examples of means for practicing the invention are described above, these examples are by no means exhaustive of all possible means for practicing the invention. The scope of the invention should therefore be determined with reference to the appended claims, along with the full range of equivalents to which those clams are entitled.

What is claimed is:

1. A method of preventing or reducing the severity of renal damage due to a blood-borne substance that is toxic to the kidneys of a human or veterinary patient, the method comprising the steps of:
   positioning an endovascular heat exchange device in a blood vessel of the patient; and
   using the endovascular heat exchange device to cool at least the patient's kidneys to a temperature at which the substance-induced renal damage is prevented or reduced in severity.

2. A method according to claim 1 wherein the endovascular heat exchange device is a catheter having a heat exchange region.

3. A method according to claim 1 wherein the endovascular heat exchange device is a catheter having a heat exchange region, the heat exchange region comprising at least one heat exchange balloon through which heat exchange fluid is circulated.

4. The method of claim 3, further comprising a step of inflating the heat exchange balloon by circulating heat exchange fluid therethrough.

5. A method according to claim 1 wherein the endovascular heat exchange device comprises a heat exchange region that is metallic.

6. A method according to claim 1 further comprising a step of disrupting laminarity of blood flow around the endovascular heat exchange device.

7. A method according to claim 1 wherein the endovascular heat exchange device is positioned proximate the patient's heart to cause a reduction in the temperature of the blood flowing through the patient's heart.

8. A method according to claim 1 wherein the step of reducing the patient's temperature is performed prior to administering the substance to the patient.

9. A method according to claim 1 further comprising a step of maintaining the reduced temperature of the patient during the administration of the substance to the patient.

10. A method according to claim 1 further comprising a step of maintaining the reduced temperature after the administration of the substance to the patient.

11. A method according to claim 1 wherein the patient's body temperature is reduced below 37 degrees Celsius.

12. A method according to claim 1 wherein the patient's body temperature is reduced to a temperature between 32 degrees Celsius and 37 degrees Celsius.

13. A method according to claim 1 further comprising a step of administering an anti-shivering treatment to the patient to reduce shivering caused by reducing the temperature of the endovascular heat exchange device.

14. The method of claim 13, wherein the anti-shivering treatment is a blanket.

15. The method of claim 13, wherein the anti-shivering treatment is an anti-shivering agent.

16. A method according to claim 1 wherein the kidney damage is the result of the administration of radiographic contrast medium.

17. A method according to claim 1 wherein the kidney damage is contrast medium-induced nephropathy.

18. A method according to claim 1 wherein the kidney damage is due to the ingestion, absorption, formation or exposure to a nephrotoxic drug or substance.

19. A method according to claim 18 wherein the nephrotoxic drug or substance is selected from the group consisting of non-steroidal antiinflamatory drugs (NSAID's), amphotericin, cisplatin, methotrexate, acyclovir, gentamicin, acetylcholinesterase inhibitors, other nephrotoxic drugs, products of tumor lysis, products of sepsis, products of infection, and products of rhabdomyolysis.

20. A method according to claim 19 wherein the patient has received an overdose of a nephrotoxic drug or substance and wherein the method further comprises the step of:
   making at least a preliminary diagnosis of overdose with a nephrotoxic substance prior to using the endovascular heat exchange device to cool at least the patient's kidneys.

21. The method of claim 20, comprising reducing the temperature of the patient's kidneys to a temperature that reduces ischemic injury of the kidney.

22. The method of claim 20, comprising reducing the patient's temperature to a temperature between 32 degrees Celsius and 37 degrees Celsius.

23. The method of claim 20, further comprising a step of administering an anti-shivering treatment to the patient.

24. The method of claim 23, wherein the anti-shivering treatment is an anti-shivering agent selected from the group consisting of: dopamine receptor blockers; dopamine receptor agonists; kappa opioid receptor agonists; opioid agonist-antagonist analgesics; serotonin 5HT1a receptor agonists; and their pharmaceutically acceptable salts.

25. A method according to claim 1 wherein a kidney or a portion of the body including a kidney is cooled and wherein the method further comprises:
    positioning a first endovascular heat exchange device in a first blood vessel of the patient through which blood flows to at least one of the patient's kidneys;
    positioning a second endovascular heat exchange device in a second blood vessel of the patient through which blood flows from at least one of the patient's kidneys;
    using the first endovascular heat exchange device to cool blood flowing to at least one of the patient's kidneys; and,
    using the second endovascular heat exchange device to warm blood flowing from at least one of the patient's kidneys.

26. A method according to claim 1 wherein a kidney or a portion of the body including a kidney is cooled and wherein the method further comprises:
    positioning a first endovascular heat exchange device in the aorta upstream of the location at which a renal artery branches from the aorta;
    positioning a second endovascular heat exchange device in the aorta downstream of said location at which a renal artery branches from the aorta;
    using the first endovascular heat exchange device to cool blood flowing through the aorta, a portion of which flows into the renal artery; and,
    using the second endovascular heat exchange device to warm the remaining blood flowing through the aorta after the portion has flowed into the renal artery.

27. A method according to claim 1 further comprising a step of monitoring the temperature of the patient.

28. A method according to claim 1 further comprising steps of:
    monitoring the temperature of the patient; and
    adjusting the temperature of the heat exchange catheter based on the temperature so monitored.

29. A method for preventing or reducing the severity of kidney damage in a human or veterinary patient due to the administration, ingestion, absorption or production of, or exposure to, a nephrotoxic substance, said method comprising the steps of:
    providing a heat exchange catheter that has a heat exchanger which is positionable within a blood vessel of the patient and a controller that controls the temperature of the heat exchanger;
    positioning the heat exchanger in a blood vessel of the patient without entirely preventing the flow of blood around the heat exchanger; and
    controlling the temperature of the heat exchanger to reduce the temperature of the patient's blood and to cool the patient's kidneys, thereby preventing or reducing the severity of kidney damage.

30. The method of claim 29, wherein the patient's kidneys are cooled prior to the administration of the substance to the patient.

31. The method of claim 29, wherein the patient's kidneys are cooled during the administration of the substance to the patient.

32. The method of claim 29, wherein the patient's kidneys are cooled after the administration of the substance to the patient.

33. The method of claim 29, further comprising the step of maintaining the reduction in temperature during the administration of the substance to the patient.

34. The method of claim 29, wherein the heat exchange catheter comprises at least one balloon containing a heat exchange fluid.

35. The method of claim 34, wherein the heat exchange catheter is positioned in the patients inferior or superior vena cava.

36. The method of claim 34, wherein the at least one balloon is disposed at the distal end of the heat exchange catheter.

37. The method of claim 29, further comprising a step of disrupting the laminar flow of blood around the heat exchange catheter.

38. The method of claim 37, wherein the laminar flow of blood is disrupted by one or more fins provided on the heat exchange catheter.

39. The method of claim 29, wherein the heat exchange catheter is positioned in the patient's venous system.

40. The method of claim 29, further comprising a step of monitoring the temperature of the patient.

41. The method of claim 29, further comprising steps of:
    monitoring the temperature of the patient; and
    adjusting the temperature of the heat exchange catheter based on the temperature so monitored.

42. A system for preventing or reducing the severity of renal damage due to a blood-borne substance that is toxic to the kidneys of a human or veterinary patient, said system comprising:
    a heat exchange catheter insertable into a blood vessel of the patient; and
    a temperature controller in communication with the heat exchange catheter to cause the heat exchange catheter to reduce the temperature of at least the a patient's kidneys to a temperature at which the substance-induced renal damage is prevented or mitigated; and
    an anti-shivering element comprising a quantity of an anti-shivering agent and apparatus for administering that anti-shivering agent to the patent.

43. The system of claim 42, wherein the heat exchange catheter comprises at least one balloon containing a heat exchange fluid flowing from the temperature controller.

44. The system of claim 42, wherein the at least one balloon is circumferentially disposed about the catheter to direct the heat exchange fluid in an opposite direction of blood flowing past the catheter.

45. The system of claim 42, wherein the temperature controller includes
    temperature monitoring means for monitoring the patient's temperature; and
    temperature adjusting means for adjusting the temperature of the heat exchange catheter to maintain a constant reduced temperature of the patient's kidneys.

46. The system of claim 45, wherein the temperature adjusting means adjusts the temperature in response to the temperature monitored by the temperature monitoring means.

47. The system of claim 42, wherein the heat exchange catheter comprises a flow disruption device to disrupt the laminarity of blood flow around the catheter.

48. The system of claim 42, wherein the temperature controller controls the temperature and flow of heat exchange fluid flowing through the heat exchange catheter.

49. The system of claim 42 wherein the anti-shivering agent is selected from the group consisting of: dopamine receptor blockers; dopamine receptor agonists; kappa opioid receptor agonists; opioid agonist-antagonist analgesics; serotonin 5HT1a receptor agonists; and their pharmaceutically acceptable salts.

* * * * *